United States Patent [19]

Taylor et al.

[11] Patent Number: 5,653,707
[45] Date of Patent: Aug. 5, 1997

[54] EXTERNAL SKELETAL FIXATION SYSTEM WITH IMPROVED BAR-TO-BAR CONNECTOR

[75] Inventors: Harold S. Taylor; J. Charles Taylor, both of Memphis, Tenn.

[73] Assignee: Smith & Nephew Richards, Inc., Memphis, Tenn.

[21] Appl. No.: 332,698

[22] Filed: Nov. 1, 1994

[51] Int. Cl.⁶ .................................................. A61B 17/60
[52] U.S. Cl. .................................................................. 606/54
[58] Field of Search .................................. 606/54, 55, 56, 606/57, 58, 59, 72, 73, 86, 105; 602/12, 16, 20, 23

[56] References Cited

U.S. PATENT DOCUMENTS

| | | |
|---|---|---|
| 2,250,417 | 7/1941 | Ettinger . |
| 2,391,537 | 12/1945 | Anderson . |
| 2,687,720 | 8/1954 | Haboush ................... 606/54 X |
| 3,941,123 | 3/1976 | Volkov et al. . |
| 4,033,340 | 7/1977 | Kalnberz . |
| 4,100,919 | 7/1978 | Oganesyan et al. . |
| 4,349,017 | 9/1982 | Sayegh ....................... 606/54 X |
| 4,361,144 | 11/1982 | Slätis et al. . |
| 4,483,334 | 11/1984 | Murray . |
| 4,541,422 | 9/1985 | de Zbikowski . |
| 4,615,338 | 10/1986 | Ilizarov et al. . |
| 4,620,533 | 11/1986 | Mears . |
| 4,628,922 | 12/1986 | Dewar ....................... 606/54 X |
| 4,662,365 | 5/1987 | Gotzen et al. . |
| 4,889,111 | 12/1989 | Ben-Dov . |
| 5,062,844 | 11/1991 | Jamison et al. ............. 606/54 |
| 5,209,750 | 5/1993 | Stef ........................... 606/54 |
| 5,219,349 | 6/1993 | Krag et al. .................. 606/53 |
| 5,429,637 | 7/1995 | Hardy ........................ 606/54 |

FOREIGN PATENT DOCUMENTS

| | | | |
|---|---|---|---|
| 393346 | 10/1990 | European Pat. Off. ................... 606/54 |
| 3614305 | 11/1987 | Germany ................................... 606/54 |
| 1519673 | 7/1989 | U.S.S.R. . |
| 1591969 | 9/1990 | U.S.S.R. ...................................... 606/54 |
| 2077847 | 12/1981 | United Kingdom . |
| 9202185 | 2/1992 | WIPO ........................................ 606/54 |

OTHER PUBLICATIONS

Richards Medical Company, *Richards External Fixation Systems*, 1983, 8 pgs. author unknown.

Pfizer Hospital Products Group, Inc. (Howmedica), *Monticelli Spinelli External Fixation System*, 1991, front & back covers and pp. 1–28, author unknown.

Richards Medical Company, *The Ilizarov External Fixator General Surgical Technique Brochure*, 1988, cover & p. 17, author unknown.

Aspen Publishers, *Techniues in Orthopaedics—Basic Ilizarov Techniques*, vol. 5 No. 4, Dec. 1990, cover & pp. 57–58, author unknown.

*Hex—Fix Surgical Technique* brochure, Title page & pp. 1–7. author and date unknown.

*Primary Examiner*—Guy V. Tucker
*Attorney, Agent, or Firm*—Earl Douglas; Larry McKenzie

[57] ABSTRACT

An improved connector for an external skeletal fixation system of the type including a first elongated bar having a longitudinal axis and a non-circular cross section and including a second elongated bar having a longitudinal axis. The connector includes a body having a first aperture therethrough for receiving the first elongated bar and having a second aperture therethrough for receiving the second elongated bar. The first aperture has a cross section that is at least partly congruent with the cross section of the first elongated bar for receiving the first elongated bar and for preventing rotation of the first elongated bar about the longitudinal axis of the first elongated bar.

10 Claims, 3 Drawing Sheets

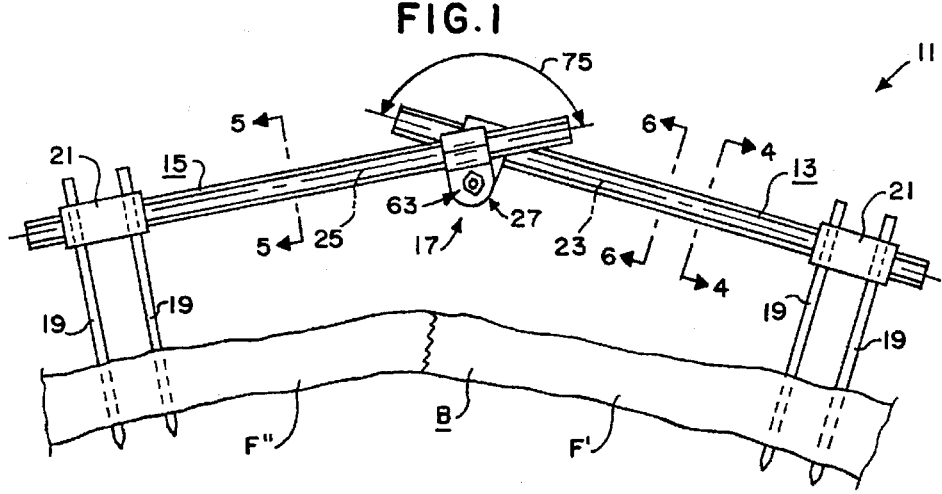
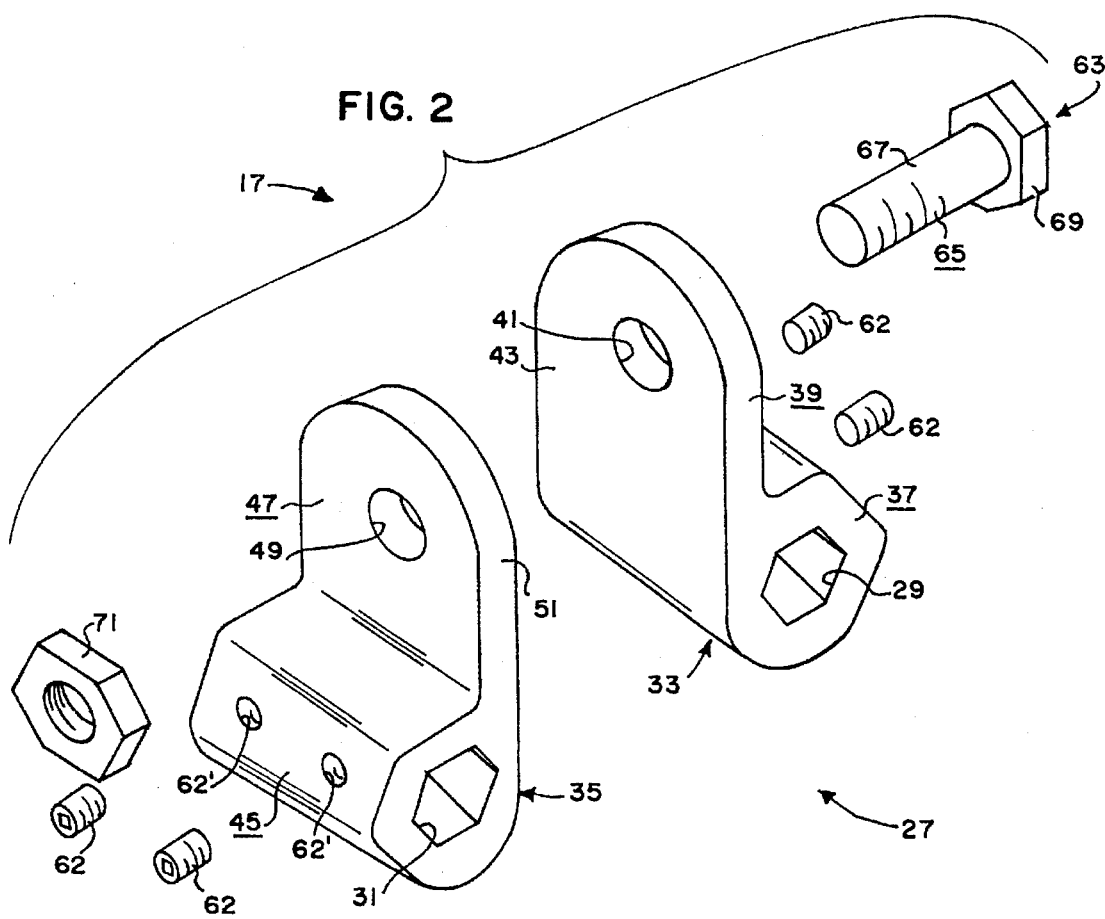

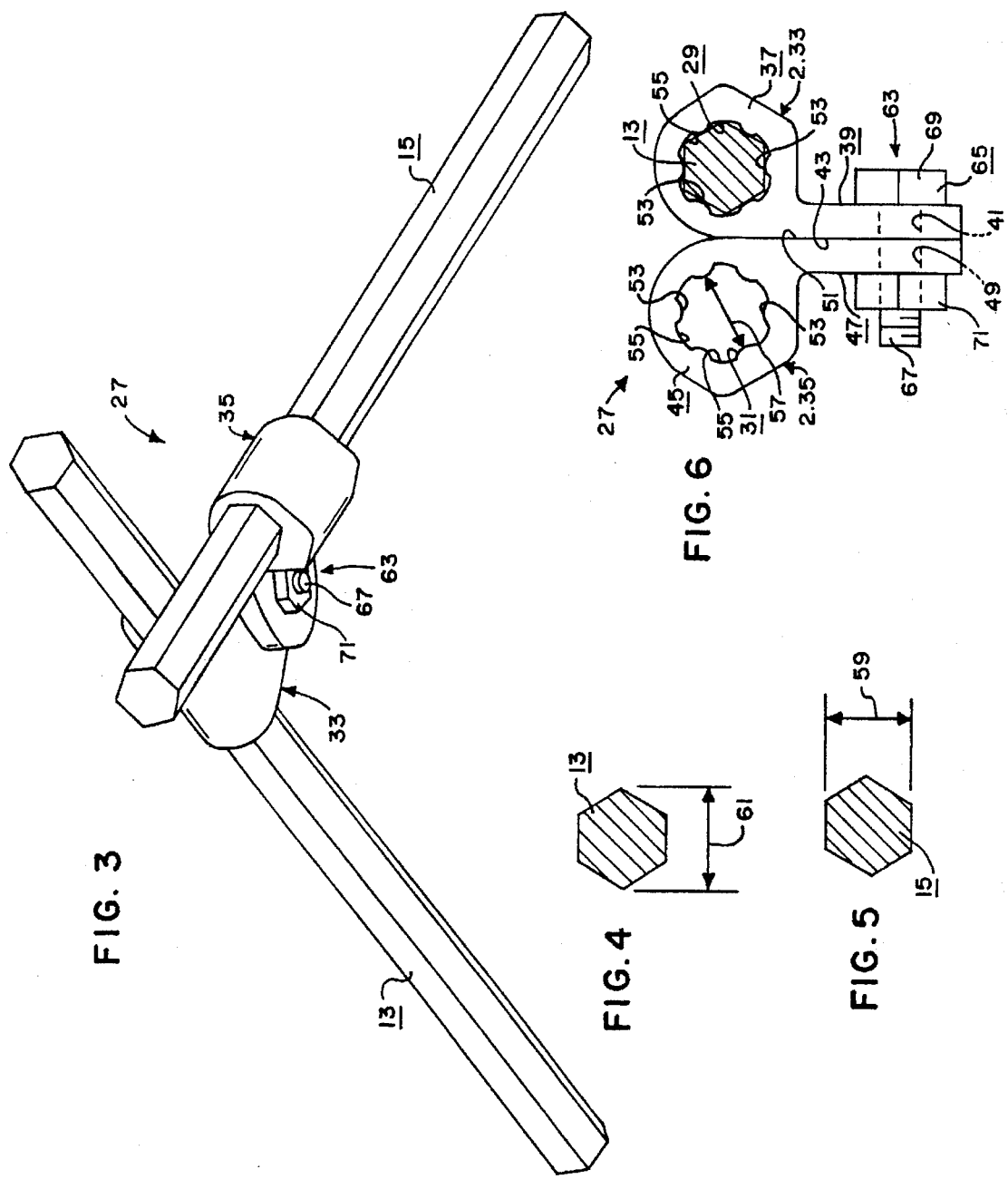

EXTERNAL SKELETAL FIXATION SYSTEM WITH IMPROVED BAR-TO-BAR CONNECTOR

BACKGROUND OF THE INVENTION

1. Field of the Invention

The present invention relates, in general, to external skeletal fixation systems and, more specifically, to an external skeletal fixation system including improved means for connecting a first external fixation bar to a second external fixation bar, etc., in a manner which prevents at least one of the external fixation bars from rotating about its longitudinal axes.

2. Description of the Related Art

Fractures of bone structure can be treated surgically, inter alia, by external fixation, by internal fixation, or by osteosynthesis. External fixation is commonly utilized to treat acute fractures of the skeleton, soft tissue injuries, delayed union of the skeleton when bones are slow to heal, nonunion of the skeleton when bones have not healed, malunion whereby broken or fractured bones have healed in a malposition, congenital deformities whereby bones develop a malposition, and bone lengthening, widening, or twisting.

External fixation systems typically include an elongated external frame, a plurality of threaded and/or smooth pins and/or threaded and/or smooth and/or beaded wires, etc., for attaching to bone structure; and a plurality of external fixation connectors for attaching the pins or wires, etc., to the external fixation frame at desired locations along the length of the frame. The pins or wires may extend completely through the boney skeleton extending out each side of the limb (commonly referred to as "transfixation pins") or may extend through the boney skeleton and out only one side of the limb (commonly referred to as "half pins").

External fixation frames vary considerably in design and capabilities, and may include multiple or single elongated bars or rods for extending generally longitudinally of the boney skeleton; rings or plates for encircling a portion of the boney skeleton, etc. Materials for frames also vary, including metals, alloys, plastics, composites, and ceramics. External fixation frames vary in their ability to accommodate different spatial relations between the pin and bar.

Murray, U.S. Pat. No. 4,483,334, issued Nov. 20, 1984, discloses an external fixation frame including a plurality of bone pins secured to a fractured bone and attached to a plurality of bars by a plurality of connectors. The bars are circular in cross sectional shape and each connector has a slot extending to a circular aperture for receiving one of the bars. A screw extends through each slot in such a manner that tightening the screw will squeeze the circular aperture about the circular bar to secure the bar to the connector.

de Zbikowski, U.S. Pat. No. 4,541,422, issued Sep. 17, 1985, discloses an external fixation frame including a plurality of transfixation pins extending through a fractured bone and attached to a telescopic bar by articulated joints. At least the portion of the bar that is connected to an articulated joint is circular in cross section and each articulated joint has a slot extending to a circular aperture for receiving a bar. A screw extends through the slot in such a manner that tightening the screw will squeeze the circular aperture about the circular portion of the bar to secure the bar to the articulated joint.

Mears, U.S. Pat. No. 4,620,533, issued Nov. 4, 1986, discloses an external fixation frame including a plurality of fixation pins inserted through a fractured bone and attached to a rigid bar through adjustable clamps. Each clamp includes an articulating ball having an axial hole through which a pin extends and having radial slots to allow for compression and consequent locking of the pin when screws are tightened. Mears also discloses a bar-to-bar clamp for coupling one rigid bar to a second rigid bar. Each bar is circular in cross section and the bar-to-bar clamp has a slot which extends to a first circular hole for receiving the first bar and a slot which extends to a second circular hole for receiving the second bar. A screw extends through both slots so that when the screw is tightened, the circular holes will be squeezed about the circular bars to secure the bars to the clamp.

Shearer et al., British Patent 2 077 847 A, issued Jun. 12, 1980, discloses an external fixation frame including a plurality of fixation pins inserted through a fractured bone and attached to a pair of rigid bars through connectors. The bars are connected together by a block having a pair of bores. Each bore is adapted to receive the spherical head of one of the bars. A screw-type vice or clamp mechanism is associated with each bore to squeeze opposing sleeve or jaw members against opposite surfaces of one of the spherical heads to secure the bars to the block.

Nothing in the known prior art discloses or suggests the present invention. More specifically, nothing in the known prior art discloses or suggests an improved connector for an external skeletal fixation system of the type including a first elongated bar having a longitudinal axis and a non-circular cross section and including a second elongated bar having a longitudinal axis; the connector including a body having a first aperture therethrough for receiving the first elongated bar and having a second aperture therethrough for receiving the second elongated bar; the first aperture having a cross section that is at least partly congruent with the cross section of the first elongated bar for receiving the first elongated bar and for preventing rotation of the first elongated bar about the longitudinal axis of the first elongated bar.

SUMMARY OF THE INVENTION

The present invention provides a connector for connecting a pair of external fixation bars of an orthopedic external fixation system together in a manner which prevents rotation of at least one of the bars about its longitudinal axes. A basic concept of the present invention is to provide an improved connector for an external skeletal fixation system of the type including a first external fixation bar having a longitudinal axis and a non-circular cross section and including a second external fixation bar having a longitudinal axis with a body having a first non-circular aperture therethrough that is at least partly congruent with the cross section of the first elongated bar for receiving the first elongated bar whereby rotation of the first elongated bar about its respective longitudinal axes is prevented and having a second aperture therethrough for receiving the second elongated bar.

One object of the present invention is to provide an orthopedic external fixation system with an improved bar-to-bar connector which allows two or more external fixation bars to be connected together in a manner which prevents one or both bars from rotating about their longitudinal axes.

Another object of the present invention is to provide such an improved bar-to-bar connector which allows the bars to be pivoted or angled relative to one another about an axis transverse to their longitudinal axes.

Another object of the present invention is to provide such an improved bar-to-bar connector which allows the length or overlap of the bars relative to one another to be adjusted.

Another object of the present invention is to provide such an improved bar-to-bar connector which maintains the angle between bars while bar length is adjusted by translating within the connector.

Another object of the present invention is to provide such an improved bar-to-bar connector which maintains the length of each bar while the angle between the bars is changed.

Another object of the present invention is to provide such an improved bar-to-bar connector which allows the angle and length relationship of the bars to be maintained.

Another object of the present invention is to provide such an improved bar-to-bar connector which prevents rotation of either bar within the connector while length or angle between the bars is changed.

BRIEF DESCRIPTION OF THE DRAWINGS

FIG. 1 is a diagrammatic elevation view of the orthopedic external fixation system of the present invention shown diagrammatically in combination with a fractured bone.

FIG. 2 is an exploded perspective view of the improved bar-to-bar connector of the external fixation system of the present invention showing a first embodiment of the body member of the improved bar-to-bar connector.

FIG. 3 is a perspective view of the improved bar-to-bar connector of the external fixation system of the present invention showing the first embodiment of the body member of the improved bar-to-bar connector in combination with a pair of external fixation bars of the external fixation system of the present invention.

FIG. 4 is a sectional view substantially as taken on line 4—4 of FIG. 1 with portions thereof omitted for clarity.

FIG. 5 is a sectional view substantially as taken on line 5—5 of FIG. 1 with portions thereof omitted for clarity.

FIG. 6 is a somewhat diagrammatic sectional view substantially as taken on line 6—6 of FIG. 1 but showing a second embodiment of the body members of the body of the improved bar-to-bar connector of the external fixation system of the present invention somewhat enlarged and with portions thereof omitted for clarity.

DESCRIPTION OF THE PREFERRED EMBODIMENTS

Figure 7:
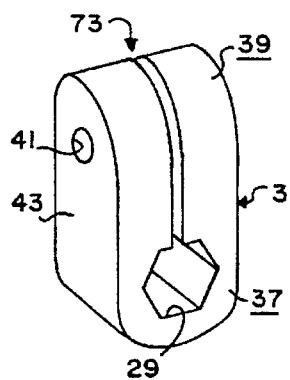
FIG. 7 is a perspective view of a third embodiment of a body member of the body of the improved bar-m-bar connector of the external fixation system of the present invention.

A preferred embodiment of the orthopedic external fixation system of the present invention is shown in FIG. 1, and identified by the numeral 11. The orthopedic external fixation system 11 is shown in FIG. 1 as providing external skeletal fixation of first and second bone fragments F', F" of bone structure B, such as a human femur. The external fixation system 11 shown in FIG. 1 includes a first elongated external fixation bar or rod 13, a second elongated external fixation bar or rod 15, and an improved bar-to-bar connector 17 for connecting the first and second elongated bars 13, 15 to one another. The external fixation system 11 may include a plurality of external fixation pins 19 for being secured to the bone structure B, and a plurality of external fixation pin connectors 21 for connecting the pins 19 to the bars 13, 15 at spaced locations thereon as shown in FIG. 1, or the like, whereby desired force can be applied between the first and second bone fragments F', F", etc., as will now be apparent to those skilled in the art. It should be understood that the number and type of pins 19 and connectors 21, or the like, may vary depending on the bone structure, etc., as will now be apparent to those skilled in the art.

The first elongated bar 13 preferably consists of rigid, elongated member having a longitudinal axis 23 and a non-circular cross section. More specifically, the first elongated bar 13 preferably has a hexagonal cross section as clearly shown in FIG. 4. The first elongated bar 13 could have some other non-circular cross section such as, for example, a generally circular cross section with one or more flats machined or otherwise formed thereon. The length, cross sectional shape size, rigidity, etc., of the first elongated bar 13 can vary depending on the intended use of the system 11, etc., as will now be apparent to those skilled in the art.

The second elongated bar 15 preferably consists of rigid, elongated member having a longitudinal axis 25 and a non-circular cross section. More specifically, the second elongated bar 15 preferably has a hexagonal cross section as clearly shown in FIG. 5. The second elongated bar 15 could have some other non-circular cross section such as, for example, a generally circular cross section with one or more flats machined or otherwise formed thereon. The length, cross sectional shape and size, rigidity, etc., of the second elongated bar 15 can vary depending on the intended use of the system 11, etc., as will now be apparent to those skilled in the art.

The improved bar-to-bar connector 17 includes a body 27 having a first aperture 29 therethrough for receiving the first elongated bar 13 and having a second aperture 31 therethrough for receiving the second elongated bar 15. The first aperture 29 has a cross section that is at least partly congruent with the cross section of the first elongated bar 13. That is, the cross section of the first aperture 29 at least partly matches the cross section of the first elongated bar 13 so that the first elongated bar 13 can be easily inserted into the first aperture 29 and so that the first elongated bar 13 cannot be rotated about its longitudinal axis 23 after being inserted into the first aperture 29. The second aperture 31 has a cross section that is at least partly congruent with the cross section of the second elongated bar 15. That is, the cross section of the second aperture 31 at least partly matches the cross section of the second elongated bar 15 so that the second elongated bar 15 can be easily inserted into the second aperture 31 and so that the second elongated bar 15 cannot be rotated about its longitudinal axis 25 after being inserted into the second aperture 31.

The body 27 preferably includes a first body member and a second body member. The first aperture 29 preferably extends through the first body member and the second aperture 31 preferably extends through the second body member.

A first embodiment of the first body member of the body 27 of the improved bar-to-bar connector 17 is clearly shown in FIG. 2 and identified by the numeral 33. The first body member 33 preferably includes a somewhat tubular portion 37 forming the first aperture 29 and a tab portion 39 extending from the tubular portion 37. The tab portion 39 preferably has an aperture 41 extending therethrough. The longitudinal axis of the aperture 41 may be transverse to the longitudinal axis of the first aperture 29. The tab portion 39 has a face side 43. The face side 43 of the tab portion 39 may be substantially flat. The first body member 33 may be machined or otherwise constructed out of a strong, substantially rigid material such as stainless steel or the like in various sizes and specific designs.

A first embodiment of the second body member of the body 27 of the improved bar-to-bar connector 17 is clearly shown in FIG. 2 and identified by the numeral 35. The second body member 35 preferably includes a somewhat tubular portion 45 forming the second aperture 31 and a tab portion 47 extending from the tubular portion 45. The tab portion 47 preferably has an aperture 49 extending therethrough. The longitudinal axis of the aperture 49 may be transverse to the longitudinal axis of the second aperture 31. The tab portion 47 has a face side 51. The face side 51 of the tab portion 47 may be substantially flat. The second body member 35 may also be machined or otherwise constructed out of a strong, substantially rigid material such as stainless steel or the like in various sizes and specific designs.

In the first embodiment of the body members 33, 35, the cross section of the apertures 29, 31 exactly correspond with the cross section of the bars 13, 15 in such a manner that each bar 13, 15 can be easily slid back and forth in the respective aperture 29, 31 while the bars 13, 15 are prevented from rotating about their respective longitudinal axes 23, 25 relative to the apertures 29, 31 after being inserted into the apertures 29, 31. Thus, as clearly shown in FIG. 2, the apertures 29, 31 of the first embodiment of the body members 33, 35 are preferably hexagonal in cross section and the same size, or only slightly larger, in cross sectional size than the bars 13, 15. Means such as set screws 62 and coacting threaded apertures 62' or the like are preferably provided for selectively locking or fixedly securing the bars 13, 15 to the respective body member 33, 35 in a manner as will now be apparent to those skilled in the art.

The improved bar-to-bar connector 17 preferably includes attachment means for attaching the first and second body members 33, 35 relative to one another. A preferred embodiment of the attachment means is shown generally in FIGS. 1, 2, 3, 6, 8 and 10 and identified by the numeral 63. The attachment means 63 preferably includes a bolt member 65 having a shaft 67 for extending through the aperture 41 in the tab portion 39 of the first body member 33 and through the aperture 49 in the tab portion 47 of the second body member 35 and having a head 69, and preferably includes a nut member 71 for screwably coacting with the shaft 67 of the bolt member 65 to attach the first and second body members 33, 35 to one another with the face sides 43, 51 of the first and second body members 33, 35 abutting one another as will now be apparent to those skilled in the art. The bolt and nut members 65, 71 may be typical, off-the-shelf components. Other embodiments of the attachment means may include cam action clamps, etc., as will now be apparent to those skilled in the art. In addition, one of the apertures 41, 49 may be threaded and the attachment means may consist of a bolt for extending through one of the apertures 41, 49 and for being screwed into the threaded aperture 41, 49, etc., as will now be apparent to those skilled in the art.

A second embodiment of the first and second body members of the body 27 of the improved bar-to-bar connector 17 is shown in FIG. 6 and identified, respectively, by the numerals 2.33, 2.35 and with like portions identified by the same numerals as the first embodiment of the first and second body members 33, 35. In this second embodiment, the cross sectional shape of the apertures 29, 31 correspond only in part to the cross sectional shape of the bars 13, 15 to allow the bars 13, 15 to be easily slid into the apertures 29, 31 while preventing rotation of the bars 13, 15 about their respective longitudinal axes 23, 25 relative to the apertures 29, 31 after being inserted into the apertures 29, 31. Thus, as clearly shown in FIG. 6, the wall of the apertures 31 of the second embodiment of the body members 2.33, 2.35 may be corrugated, forming alternating ridges 53 and valleys or grooves 55 with the distance 57 between opposing ridges as indicated by the arrow in FIG. 6 (hereinafter referred to as 'ridge distance')equal to or greater than the distance 59 across the flats of the bars 13, 15 as indicated by the arrow in FIG. 5 (hereinafter referred to as 'flat distance')but less than the distance 61 across the points of the bars 13, 15 as indicated by the arrow in FIG. 4 (hereinafter referred to as 'point distance')so that the bars 13, 15 can be easily inserted into the aperture 31 without requiring exact alignment of the bars 13, 15 with the aperture 31 and so that the bars 13, 15 will not rotate within the aperture 31 more than the distance between adjacent ridges 53 as will now be apparent to those skilled in the art.

Figure 8:
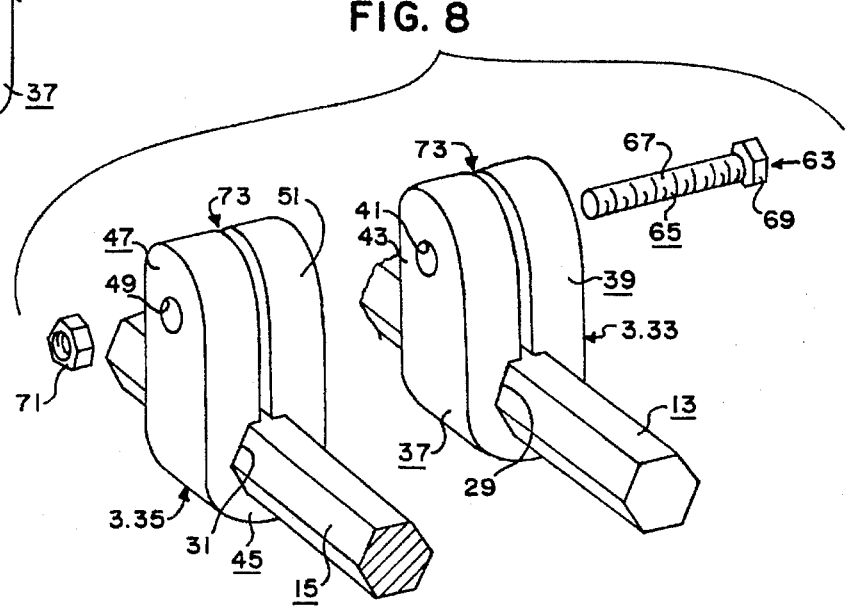
FIG. 8 is an exploded perspective view of the improved bar-to-bar connector of the external fixation system of the present invention showing the third embodiment of the body member of the improved bar-to-bar connector in combination with a pair of external fixation bars of the external fixation system of the present invention.

A third embodiment of the body members of the body 27 of the improved bar-to-bar connector 17 is shown in FIGS. 7 and 8 and identified, respectively, by the numerals 3.33, 3.35 and with like portions identified by the same numerals as the first embodiment of the first and second body members 33, 35. In this third embodiment, a slot 73 extends from the apertures 29, 31 through the tab portions 39; 49 so that when an attachment means, e.g., the attachment means 63 attaches the first and second body members 3.33, 3.35 relative to one another, the slot 73 will be compressed, securely clamping a bar 13, 15 to the respective body member 3.33, 3.35 as will now be apparent to those skilled in the art. The tab portions 39, 49 may be the same thickness as the respective tubular portions 37, 45 as clearly shown in FIGS. 7 and 8.

Figure 10:
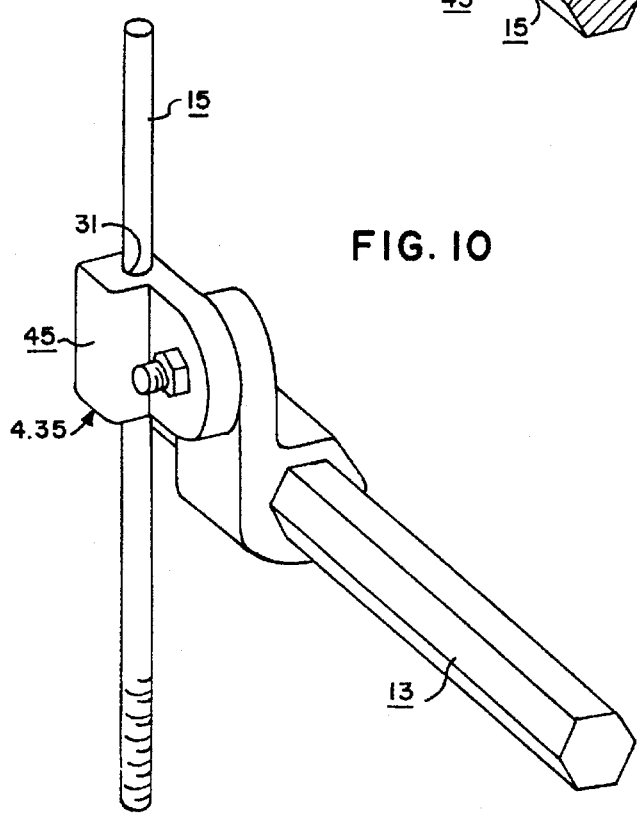
FIG. 10 is a perspective view of the improved bar-to-bar connector of the external fixation system of the present invention showing the fourth embodiment of the body member of the improved bar-to-bar connector in combination with the first embodiment of the body member and a pair of external fixation bars of the external fixation system of the present invention.
Figure 9:
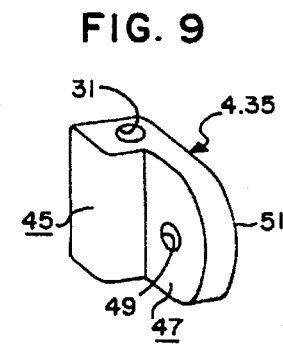
FIG. 9 is a perspective view of a fourth embodiment of a body member of the body of the improved bar-to-bar connector of the external fixation system of the present invention.

A fourth embodiment of the second body member of the body 27 of the improved bar-to-bar connector 17 is shown in FIGS. 9 and 10 and identified by the numeral 4.35 and with like portions identified by the same numerals as the first embodiment of the first and second body members 33, 35. As shown in FIG. 10, the body member 4.35 is adapted for use with the body member 33, but can be used with the body member 2.33 or the body member 3.33, etc., as will now be apparent to those skilled in the art. The body member 4.35 is designed for use to connect a typical transfixation pin or the like to the first bar 13. Thus, the second bar 15 for use with the body member 4.35 may consist of a typical transfixation pin or the like having a circular cross section. The body member 4.35 can be similar to the body member 35 but can be somewhat smaller with the aperture 31 sized for a typical transfixation pin or the like. Means such as set screws (not shown) can be provided for securing the second bar 15 to the body member 4.35 as will now be apparent to those skilled in the art.

The basic operation and use of the external fixation device 11 of the present invention is similar to the basic operation of use of prior external fixation devices. Thus, for example, to use the external fixation device 11 to provide external fixation of a bone fracture such as the fracture of the bone structure B shown in FIG. 1, fixation pins 19 are secured to the bone fragments F', F" on opposite sides of the fracture. The bars 13, 15 and fixation pins 19 are coupled to connectors 21 in the normal manner. One end of the first elongated bar 13 is inserted into the aperture 29 through the first body member 33 and secured thereto with set screws 62 or the like. One end of the second elongated bar 15 is inserted into the aperture 31 through the second body member 35 and secured thereto with set screws 62 or the like. The first and second body members 33, 35 are attached together with the attachment means 63. The angle 75 between the longitudinal axes 23, 25 as indicated by the arrow in FIG. 1 can be varied by merely pivoting or rotating the first and second body members 33, 35 about the longitudinal axis of the shaft 67 of the bolt member 65 of the attachment means 63 around the apertures 41, 49. Once the desired angle 73 is set, the bolt and nut members 65, 71 can be tightened to secure the bars 13, 15 in that position. The angle 73 can be altered as time passes for reasons as will now be apparent to those skilled in the art by merely loosening the bolt and nut members 65, 71 and rotating the body members 33, 35 about the bolt member 65. One or both bars 13, 15 can be translated within the body members 33, 35 to increase or decrease the overall bar assembly length while maintaining the set angle between the bars 13, 15 by merely loosening the set screws 62 and moving one or both bars 13, 15 within the respective body member 33, 35.

Although the present invention has been described and illustrated with respect to preferred embodiments and preferred uses therefor, it is not to be so limited since modifications and changes can be made therein which are within the full intended scope of the invention.

We claim:

1. An external skeletal fixation system comprising:
   a first external fixation bar having a longitudinal axis and a substantially hexagonal cross section;
   a second external fixation bar having a longitudinal axis and a substantially hexagonal cross section; and
   a connector that interconnects said first and second external fixation bars, said connector including:
      a first member having a first aperture therethrough for receiving said first bar, said first aperture having a substantially hexagonal cross section that is substantially identical in size and shape to the cross section of said first fixation bar; and
      a second member having a second aperture therethrough for receiving said second bar, said second aperture having a substantially hexagonal cross section that is substantially identical in size and shape to the cross section of said second fixation bar;
   wherein said first and second members are pivotally interconnected such that the angle between the longitudinal axes of the first and second bars is variable.

2. The external skeletal fixation system of claim 1, wherein the position of said connector along the longitudinal axes of said first bar and said second bar is variable.

3. The external skeletal fixation system of claim 2, wherein said connector further comprises a lock to selectively secure the position of said connector along the longitudinal axes of said first bar and said second bar.

4. The external skeletal fixation system of claim 1, wherein said connector further comprises a lock to selectively secure the position of said first member relative to said second member.

5. The external skeletal fixation system of claim 1, wherein the position of said connector along the longitudinal axes of said first bar and said second bar is variable, and said connector further comprises:
   a first lock to selectively secure the position of said connector along the longitudinal axes of said first bar and said second bar, and
   a second lock to selectively secure the position of said first member relative to said second member.

6. An external skeletal fixation system comprising:
   a first external fixation bar having a longitudinal axis;
   a second external fixation bar having a longitudinal axis; and
   a connector that interconnects said first and second external fixation bars such that the angle between the longitudinal axes of said first and second bars is variable, said connector including a first aperture for receiving said first bar, and a second aperture for receiving said second bar;
   wherein said first and second bars have substantially hexagonal cross sections that include a point distance and a flat distance;
   in which said first aperture includes an inner surface that is at least partially corrugated having a ridge distance that is greater than or equal to said flat distance of said first bar, and wherein said ridge distance of said first aperture is less than said point distance of said first bar; and
   in which said second aperture includes an inner surface that is at least partially corrugated having a ridge distance that is greater than or equal to said flat distance of said second bar, and wherein said ridge distance is less than said point distance of said second bar.

7. The external skeletal fixation system of claim 6, wherein the position of said connector along the longitudinal axes of said first bar and said second bar is variable.

8. The external skeletal fixation system of claim 7, wherein said connector further comprises a lock to selectively secure the position of said connector along the longitudinal axes of said first bar and said second bar.

9. The external skeletal fixation system of claim 6, wherein said connector further comprises a lock to selectively secure the position of said first member relative to said second member.

10. The external skeletal fixation system of claim 6, wherein the position of said connector along the longitudinal axes of said first bar and said second bar is variable, and said connector further comprises:
   a first lock to selectively secure the position of said connector along the longitudinal axes of said first bar and said second bar, and
   a second lock to selectively secure the position of said first member relative to said second member.

* * * * *